United States Patent [19]
Krause et al.

[11] Patent Number: 6,068,604
[45] Date of Patent: May 30, 2000

[54] CARTILAGE INDENTOR INSTRUMENT

[75] Inventors: Kenneth W. Krause, Sandown; Graham Smith, Plaistow, both of N.H.

[73] Assignee: Smith & Nephew, Inc., Memphis, Tenn.

[21] Appl. No.: 09/058,070

[22] Filed: Apr. 9, 1998

[51] Int. Cl.[7] .................................................. A61B 5/103
[52] U.S. Cl. .............................................. 600/587; 73/81
[58] Field of Search .................................... 600/587, 595, 600/550, 552, 553; 73/81, 82, 83, 87, 573

[56] References Cited

U.S. PATENT DOCUMENTS

| | | | |
|---|---|---|---|
| 4,159,640 | 7/1979 | Leveque et al. | 600/587 |
| 4,331,026 | 5/1982 | Howard et al. | 73/81 |
| 4,621,523 | 11/1986 | Shabel et al. | 73/81 |
| 5,433,215 | 7/1995 | Athanasiou et al. | 128/774 |
| 5,494,045 | 2/1996 | Kiviranta et al. | 128/774 |
| 5,503,162 | 4/1996 | Athanasiou et al. | 128/774 |
| 5,616,857 | 4/1997 | Merck, Jr. et al. | 73/82 |
| 5,673,708 | 10/1997 | Athanasiou et al. | 128/774 |
| 5,701,913 | 12/1997 | McPherson et al. | 600/587 |
| 5,879,312 | 3/1999 | Imoto | 600/587 |

OTHER PUBLICATIONS

A. C. Swann et al., "Improved Techniques for Measuring the Indentation and Thickness of Articular Cartilage", Proc Instn Mech Engrs vol. 203, 1989.

D.E.T. Shepherd et al., "A technique for measuring the compressive modulus of particular cartilage under . . . preliminary results", Proc Instn Mech Engrs vol. 211, Part H, 1997.

*Primary Examiner*—Cary O'Connor
*Assistant Examiner*—Charles Marmor, II
*Attorney, Agent, or Firm*—Fish & Richardson P.C.

[57] ABSTRACT

An instrument and technique for measuring the compressive properties of a body (e.g., articular cartilage) are disclosed. The instrument includes an elongated probe, a biasing assembly for applying a pre-determined pre-load to the body to establish a measurement reference at the predetermined pre-load, an actuator to move the elongated probe to apply a compressive force to the body, and a measurement device which measures displacement of the elongated probe relative to the measurement reference.

27 Claims, 6 Drawing Sheets

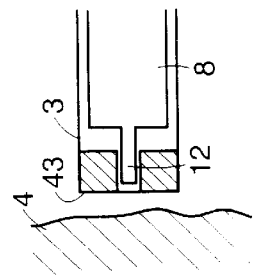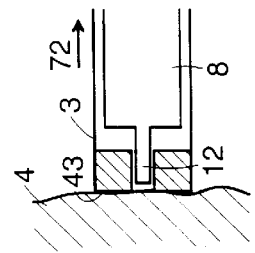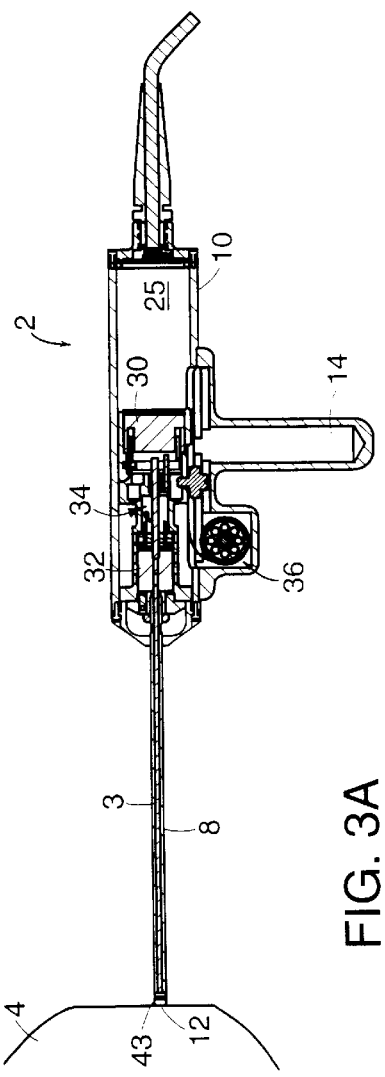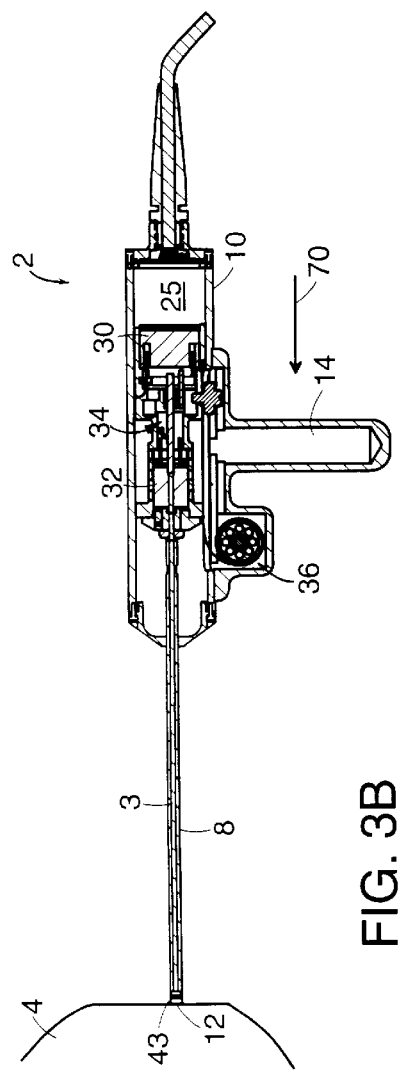

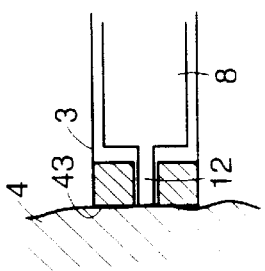
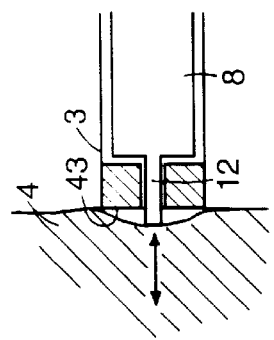
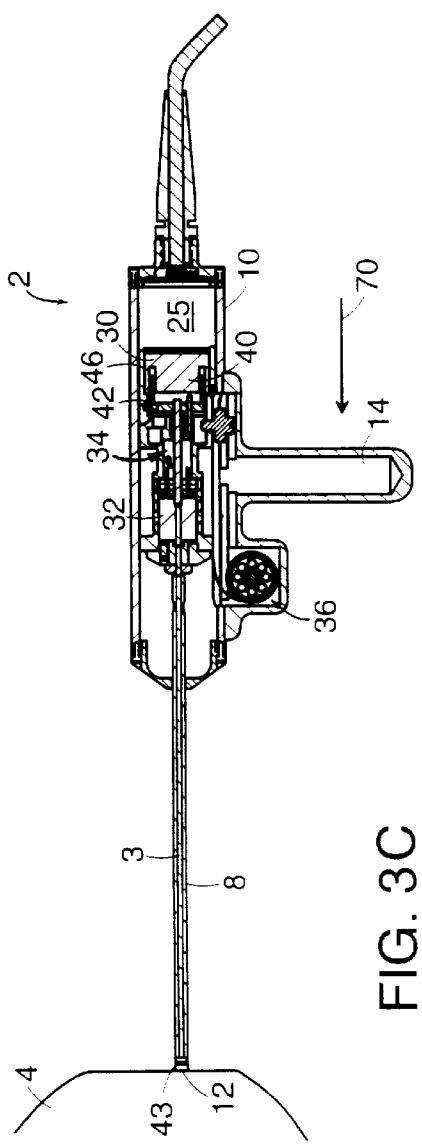
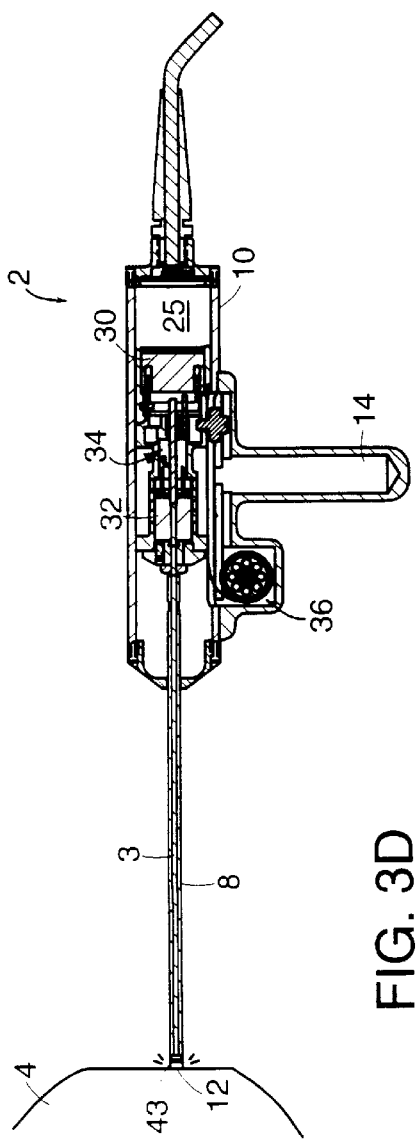

CARTILAGE INDENTOR INSTRUMENT

BACKGROUND OF THE INVENTION

This invention relates to characterizing mechanical properties of materials.

In general, the field of material mechanics is concerned with stresses and deformations of bodies. More specifically, material mechanics is generally thought of as the science which establishes the relationships between forces applied to a body and the resulting deformation of the body. The three fundamental types of stresses are tension, compression and shear. The manner in which a material responds when subjected to any or all of these stresses can be used to characterize mechanical properties of a material. For example, when a material is placed in tension, its tensile properties (e.g. tensile modulus) can be determined by measuring the deformation of the material as a function of the applied tensile stress.

A wide variety of different materials have been characterized for their mechanical properties using as many different techniques and instruments. For example, the compressive properties of articular cartilage tissue and prosthetic cartilage have been analyzed to assess the relative health of the tissue or material and the viability of the replacement material.

Articular cartilage is the bearing material in synovial joints responsible for transmitting and distributing the relatively large compressive loads arising in joints. It also provides a bearing surface with a very low coefficient of friction. As cartilage first begins to break down (e.g., due to osteoarthrosis (OA)), accurate knowledge of its mechanical properties is of great relevance. Further, knowledge of the mechanical properties is essential in attempting to produce a prosthetic cartilage for repairing surface damage of joints.

Articular cartilage is a complex structure, generally devoid of nerves and avascular, although a few blood vessels may be found in its deepest parts adjacent to the bone. Articular cartilage tissue consists of an abundant extra cellular matrix having a large amount of water (75 percent by wet weight) of which a large proportion is freely exchangeable with the synovial fluid bathing the tissue. When a compressive load is applied to articular cartilage there is an instantaneous deformation due to the elastic properties of the matrix followed by a creep phase which is due to the movement of fluid from the cartilage matrix into the surrounding synovial fluid. When the load is removed, there is an instantaneous recovery followed by a time dependent recovery before articular cartilage returns to its initial state. As the articular cartilage begins to break down, the matrix becomes less resilient. Thus, compressive property measurements can be used to distinguish healthy cartilage from unhealthy cartilage.

SUMMARY OF THE INVENTION

The invention features an instrument and a technique for measuring the compressive properties of a body (e.g., articular cartilage).

In a general aspect of the invention, the instrument includes a biasing assembly, mechanically coupled to an elongated probe, and configured to apply a pre-determined pre-load to the body and establish a measurement reference at the predetermined pre-load; an actuator for moving the elongated probe to apply a compressive force to the body; and a measurement device which measures displacement of the elongated probe in response to the compressive force relative to the measurement reference.

Among other advantages, the biasing assembly provides a pre-determined and repeatable pre-load to the body under test, thereby establishing a measurement reference point from which the displacement of the probe is measured when applying a compressive force to the body. Establishing a reference point where compressive force measurements are made eliminates operator variability and provides for accurate comparison of different measurements.

The instrument permits the compressive properties of the body material to be assessed reliably, repeatably, and quickly. For example, articular cartilage which may be subjected to substantial compressive loads during walking, running, and jumping can be characterized to determine the extent of possible osteoarthrosis. Using the instrument, the relative health of an articular cartilage sample can be assessed by measuring the compressive properties of the sample and comparing them to measurements made on healthy cartilage. In addition, prosthetic cartilage may be characterized prior to being used for replacing broken down or otherwise unhealthy cartilage.

Embodiments of this aspect of the invention may include one or more of the following features.

The biasing assembly includes a moveable member having a distal end which contacts the body and is coupled to a biasing element. For example, the moveable member may be in the form of a protective sheath surrounding the elongated probe. The biasing assembly includes a constant force spring connected to the sheath for applying the pre-load.

The actuator for moving the probe is a voice-coil actuator which applies a variable force having a magnitude which varies sinusoidally. For example, the magnitude of the sinusoidally-varied force has a frequency between 1 and 10 Hertz. The measurement device is a linear variable differential transformer (LVDT) for providing an output signal proportional to the displacement of the elongated probe.

The instrument includes a housing for enclosing the biasing assembly, the actuator, and the measurement device. The housing includes a handle for manipulating the instrument.

The instrument includes a data acquisition system that collects an output signal proportional to the displacement of the elongated probe. The data acquisition system generates data relating the output signal proportional to the displacement of the elongated probe to a known compressive force signature applied to the body. In preferred embodiments, the data acquisition system also collects an output signal proportional to the compressive force applied to the body. In these embodiments, the data acquisition system generates data relating the output signal proportional to the displacement of the elongated probe to the output signal proportional to the compressive force applied to the body. The instrument includes a monitor for displaying data relating to at least one of the applied compressive force and measured displacement.

In another aspect of the invention, a method of measuring the compressive properties of a body includes: (a) establishing a measurement reference by applying a pre-determined pre-load to the body with a biasing assembly (b) positioning a distal end of an elongated probe to contact the body; (c) applying a compressive force to the body by moving the elongated probe along a longitudinal axis of the elongated probe; and (d) measuring displacement of the elongated probe along the longitudinal axis, relative to the measurement reference, in response to the compressive force applied to the body.

Embodiments of this aspect of the invention may include one or more of the following further steps. An output signal proportional to the compressive force applied to the elongated probe is collected. Data is generated relating the output signal proportional to the displacement of the elongated probe to the output signal proportional to the compressive force applied to the body. In preferred embodiments, an output signal proportional to the displacement of the elongated probe is collected. In these embodiments, data is generated relating the output signal proportional to the displacement of the elongated probe to a known compressive force signature applied to the body. The body is, for example, a cartilage sample. The method includes comparing output signals from the body to output signals produced when the body is a healthy cartilage sample. The method includes displaying, on a monitor, data relating to at least one of the applied compressive force and measured displacement.

Other advantages and features of the invention will be apparent from the following description and from the claims.

BRIEF DESCRIPTION OF THE DRAWINGS

FIGS. 3A–3D are schematic illustrations of the cartilage indentor instrument in use.

FIGS. 4A–4D are enlarged views of portions of the illustrations of FIGS. 3A–3D.

DETAILED DESCRIPTION

Figure 1:
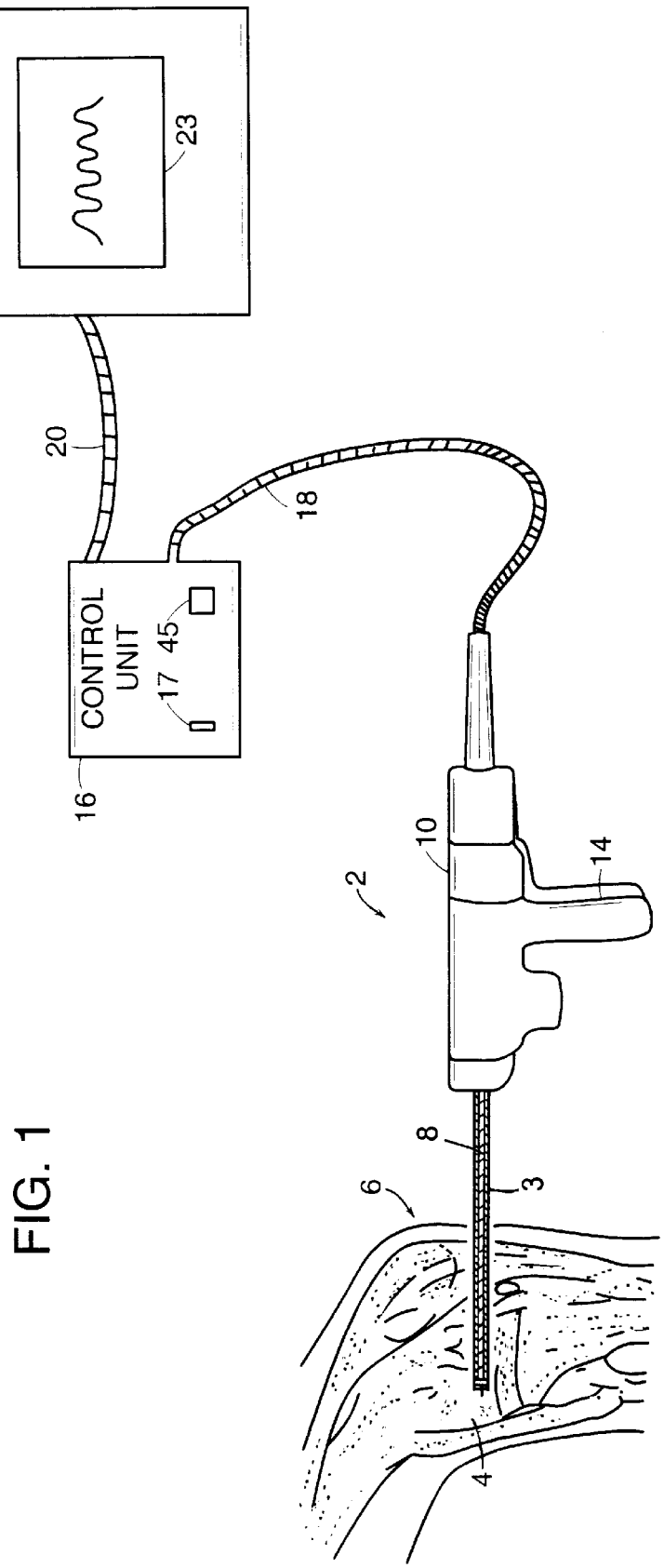
FIG. 1 is a schematic illustration of a cartilage indentor instrument for use in measuring compressive properties of cartilage.

Referring to FIG. 1, an indentor instrument 2 for measuring compressive properties of articular cartilage 4 in a joint, here a patient's knee 6, is shown. As will be discussed in greater detail below, indentor instrument 2 applies a predetermined compressive force that compresses articular cartilage 4, and measures the resulting elastic deformation as a function of the applied compressive force. The measured elastic deformation is used to characterize the quality of articular cartilage 4.

Indentor instrument 2 includes an elongated probe 8 (FIG. 2) that moves within a protective sheath 3 to apply the compressive force to articular cartilage 4. Probe 8 and sheath 3 both extend from a housing 10 having a handle 14 used to manipulate the instrument and the probe within knee 6.

A control unit 16 provides and receives, via a cable 18, electrical signals to indentor instrument 2 for generating the compressive force and measuring the deformation of articular cartilage 4, respectively. The measurement signals representative of the deformation of cartilage 4 are processed by control unit 16 and transmitted, along with the signals representative of the magnitude of the compressive force, via a cable 20, to a data acquisition system 24 for storage or further processing. Data acquisition system 24 may, for example, be used to store both the compressive force and deformation measurements as functions of time, as well as the compressive force as a function of the deformation, for the purpose of comparing the properties of different samples. Data acquisition system 24 may also include a monitor 23 to display the data (e.g., as a displacement or force waveform).

Figure 2:
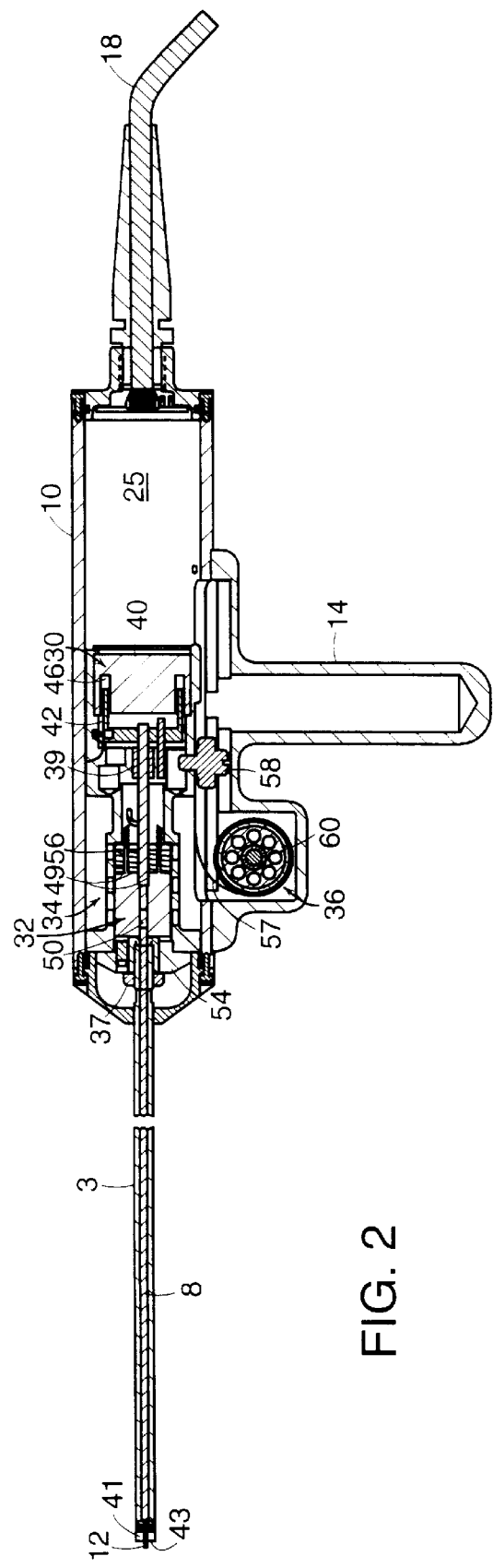
FIG. 2 is a cross-section of the cartilage indentor instrument of FIG. 1.

Referring to FIG. 2, indentor instrument 2 includes a piston-like assembly 34 which slides within a barrel-shaped interior 25 of housing 10. Probe 8 extends within piston assembly 34 and is supported by a sleeve bearing 39 which is attached to the piston assembly. Another sleeve bearing 41 supports a tip 12 of probe 8 at a distal end 43 of protective sheath 3. Tip 12 has a diameter of approximately 0.03 inches and projects slightly beyond distal end 43 of protective sheath 3 as probe 8 moves to contact articular cartilage 4 and apply the compressive force.

Piston assembly 34 includes a voice coil actuator 30 for generating an applied compressive force, and a linear variable differential transformer (LVDT) 32 for measuring the displacement of elongated probe 8 due to the deformation of the articular cartilage 4. Protective sheath 3 is secured to a distal end of piston assembly 34 with a hex nut 37.

Voice coil actuator 30 is attached to a proximal end of probe 8 and, in response to electrical current from control unit 16, causes probe 8 to apply a compressive force to articular cartilage 4. Voice coil actuator 30 includes a cylindrical permanent magnet 40 and a coil 42, which is fixed to probe 8 and suspended within a bore 46 in the permanent magnet. Coil 42 receives current from control unit 16 via cable 18. The compressive forces generated by voice coil actuator 30 result from the interactive force between the magnetic field generated by the current flowing through coil 42 and the magnetic field generated by permanent magnet 40. Coil 42 slides within bore 46 in response to the interactive force to move probe 8 longitudinally. The magnitude of the compressive force is proportional to the magnitude of the current provided to coil 42 by control unit 16.

Control unit 16 includes an interrupt timer 45 (FIG. 1) which allows for digital control of voice coil actuator 30. Over a time interval set by the operator on the interrupt timer 45, control unit 16 sends a discrete level of current to voice coil actuator 30. The current level can be changed at the end of the time interval thereby allowing the compressive force to be applied in a step-wise manner. Alternatively, control unit 16 can be configured by the operator using control switches 17 to send continuously varying, non step-wise, signals to voice coil actuator 30. To collect compressive force data as a function time, control unit 16 sends a signal proportional to the current in coil 42 at the end of each time interval to data acquisition system 24.

Articular cartilage 4 deforms in response to the compressive force applied by probe 8. The amount of deformation of articular cartilage 4 due to the compressive force is determined by measuring the displacement of probe 8. The displacement of probe 8 is measured by LVDT 32, which transmits signals proportional to the displacement of probe 8 to control unit 16 for processing. To collect deformation data as a function of time, control unit 16 sends a signal proportional to the displacement of probe 8 to data acquisition system 24 at the end of each time interval, as specified by the interrupt timer 45.

LVDT 32 is a relatively sensitive and repeatable displacement transducer having a center hole 49 through which probe 8 passes. LVDT 32 is positioned at the distal end of piston assembly 34 between a retainer cap 54 and a spring 56. LVDT 32 includes miniature primary and secondary coils (not shown) which share the same movable magnetic core. In this embodiment, the moveable magnetic core is in the form of a ferrite slug section 50 constructed within and along the length of probe 8. In general, an input signal provided by control unit 16 to a primary one of the coils in LVDT 32, induces an output signal in a pair of secondary coils in LVDT 32. Ferrite slug section 50 is disposed between the primary and secondary coils and as the slug section moves therebetween, the output of one of the secondary coils increases while the output of the other secondary coil decreases. The "out of balance" signal has a value proportional to the position of ferrite slug 50, and is used to determine the displacement of probe 8.

LVDT 32 is calibrated, for example, by extending probe 8 into a series of holes of a test body with known depths and recording electrical output signals from LVDT 32 at each depth. The relationship between the output signal measurements and the displacements of probe 8 is used to provide a calibration scale for use in future measurements.

Operator variability results from forcing tip 12 of probe 8 into articular cartilage 4 with a different compressive force prior to different measurements. An operator may push tip 12 of probe 8 into articular cartilage 4 with so large a force that articular cartilage 4 is overly compressed. On the other hand, the operator may push with a force that is insufficient for establishing contact between tip 12 and articular cartilage 4. These scenarios establish incorrect reference positions for measuring displacement and prevent accurate comparison between measurements.

To avoid these scenarios and establish an accurate and repeatable reference position, a pre-determined pre-load is applied to the cartilage through the action of a constant force spring 36 coupled to piston assembly 34. When distal end 43 of sheath 3 is pressed against articular cartilage 4, piston assembly 34 slides proximally toward the rear end of housing 10 in response to the return force from articular cartilage 4. A coil 57 of constant force spring 36 is attached to piston assembly 34 with a cam follower 58 that moves in a slot (not shown) formed along an inner surface of housing 10 as piston assembly 34 slides. Coil 56 is wrapped around a spool 60 and unwinds while maintaining a constant resistive force against the cartilage as piston assembly 34 moves proximally in barrel 25.

Constant force spring 36 provides the pre-load by resisting the motion of piston assembly 34 in response to the return force. The pre-load applied to articular cartilage 4 is equal to the resistive force provided by constant force spring 36. Constant force spring 36 is designed to provide the same resistance, independent of the position of piston assembly 34 in housing 10.

As stated above, to avoid operator variability it is important that the only resistive force applied to piston assembly 34 is that provided by constant force spring 36. This helps to ensure that the pre-load applied to articular cartilage 4 remains constant for all measurements. In order to satisfy this condition, handle 14 is pushed in a manner which moves the piston assembly 34 from its initial position along the length of barrel 25 without allowing piston assembly 34 to contact the rear wall of housing 10 which could provide an additional resistive force.

The magnitude of the pre-load is determined in advance by selecting a desired value of force to be applied by spring 36. Different materials require different pre-loads. The magnitude of the pre-load must be large enough to provide slight deformation of the material without being so large that the pre-load interferes with the measurement of the compressive properties. For example, in measuring the mechanical properties of articular cartilage, a constant spring force which applies about 0.5 Newtons is appropriate.

Data acquisition system 24 generates data relating the deformation of articular cartilage 4 to the applied compressive force in order to assess the mechanical properties of the cartilage. Graphs of deformation as a function of applied force are obtained by relating signals proportional to the displacement of probe 8 to corresponding signals proportional to the applied compressive force that are transmitted at equivalent times from LVDT 32 and control unit 16, respectively. Alternatively, it is possible for data acquisition system 24 to collect only displacement signals if the variation of applied force with time is known. The displacement signals may be stored and matched with the applied force signature, at a later time, to generate the compressive force versus deformation data.

With reference to FIGS. 3A–3D and FIGS. 4A–4D, the operation of indentor instrument 2 will be described.

Referring to FIG. 3A, an incision in the area of patient's knee 6 (FIG. 1) provides access to articular cartilage 4 for indentor instrument 2. Handle 14 on housing 10 is used to manipulate indentor instrument 2 such that sheath 3 is positioned perpendicular and proximal to the surface of articular cartilage 4 (FIG. 4A).

Referring to FIGS. 3B and 4B, a constant pre-load is applied to articular cartilage 4 prior to measuring the compressive properties by manually pushing handle 14 in the direction of arrow 70 so that distal end 43 of sheath 3 contacts and deforms articular cartilage 4. In response to the applied force, articular cartilage 4 provides a return force to sheath 3 in the direction of arrow 72 (FIG. 4B) opposite the applied force. The return force causes piston assembly 34 to move in the direction of the return force within barrel-shaped interior 25 of housing 10. Constant force spring 36 provides a resistive force and the piston assembly 34 reaches an equilibrium position within barrel-shaped interior 25 so that the pre-load on articular cartilage 4 is equivalent to the spring force.

It is important to establish an initial reference position to ensure that any measured displacement is due solely to deformation of articular cartilage 4 caused by the compressive force applied by probe 8.

Referring to FIGS. 3C and 4C, with sheath 3 in contact with articular cartilage 4 to provide the pre-load, the initial reference position of probe 8 is then established before the measurement of the compressive properties of articular cartilage 4. The reference position is established by the action of an impulse force, applied over a short time interval, from voice coil actuator 30 to set probe 8 in motion within sheath 3 toward articular cartilage 4. To apply the impulse force, the operator actuates a control switch, mounted, for example, on handle 14, a foot switch (not shown) connected to control unit 16, or the control unit itself, to an on position. A spike of current is provided to voice coil actuator 30 over a short time interval to generate the impulse force.

The magnitude of the impulse force must be large enough to provide probe 8 with enough momentum to move tip 12 to reach articular cartilage 4. Articular cartilage 4 stops the motion of probe 8 at a position at which tip 12 contacts without deforming articular cartilage 4. This position of probe 8 establishes an initial reference point from which the displacement of probe 8 is measured. The displacement of probe 8 from the reference position is equal to the deformation of articular cartilage 4 due to the compressive force applied by probe 8 during the measurement.

Referring to FIGS. 3D and 4D, after the reference position has been established, a current is supplied to voice coil actuator 30 from control unit 16 (FIG. 1) to generate a variable compressive force at a predetermined frequency causing probe 8 to reciprocate in the direction of arrow 74 (FIG. 4D) within articular cartilage 4. The current is supplied by control unit 16 in discrete time intervals (e.g. 1/32 seconds) set by interrupt timer 45 of the control unit 16. The force is varied, for example, in a manner that approaches a sinusoid, by supplying different current levels over different time intervals. At the end of each time interval, a signal is processed by control unit 16 and sent to data acquisition system 24 proportional to the current level and thus the compressive force applied to articular cartilage 4. The magnitude of the compressive force as a function of time is stored by data acquisition system 24.

LVDT 32 measures the reciprocating displacement of probe 8 from the equilibrium position, established by providing the constant pre-load. The displacement of probe 8 is equal to the deformation of articular cartilage 4 in response to the compressive force. LVDT 32 sends an output signal to control unit 16 (FIG. 1) proportional to the deformation. Referring again to FIG. 1, control unit 16 processes electrical signals proportional to the deformation at the end of each time interval, specified by interrupt timer 45, and sends the signals to data acquisition system 24. The magnitude of the deformation as a function of time is stored by data acquisition system 24.

Figure 5A:
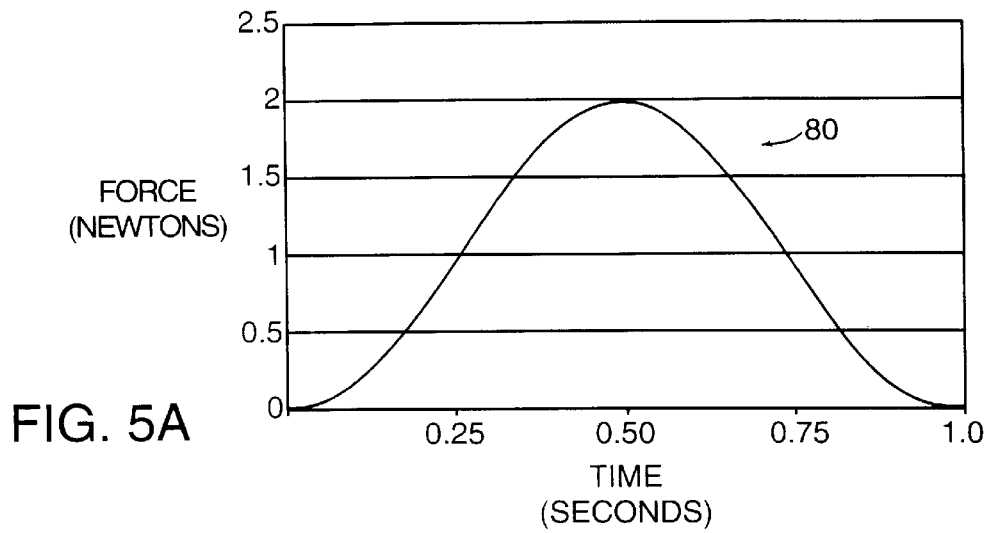
FIGS. 5A–5C are graphs of data obtained during the measurement of the compressive properties of a silicone rubber sample during a 1 Hertz cycle of the measurement.
Figure 5B:
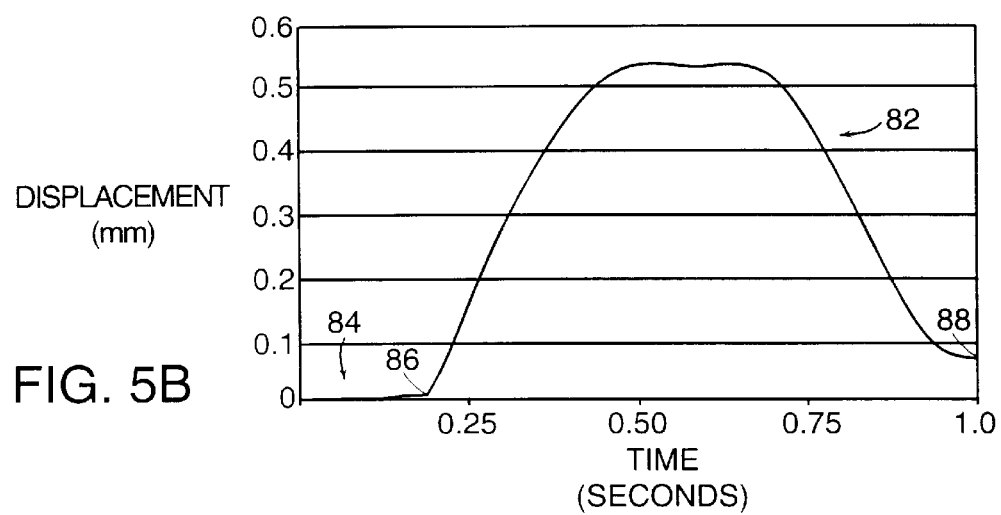
Figure 5C:
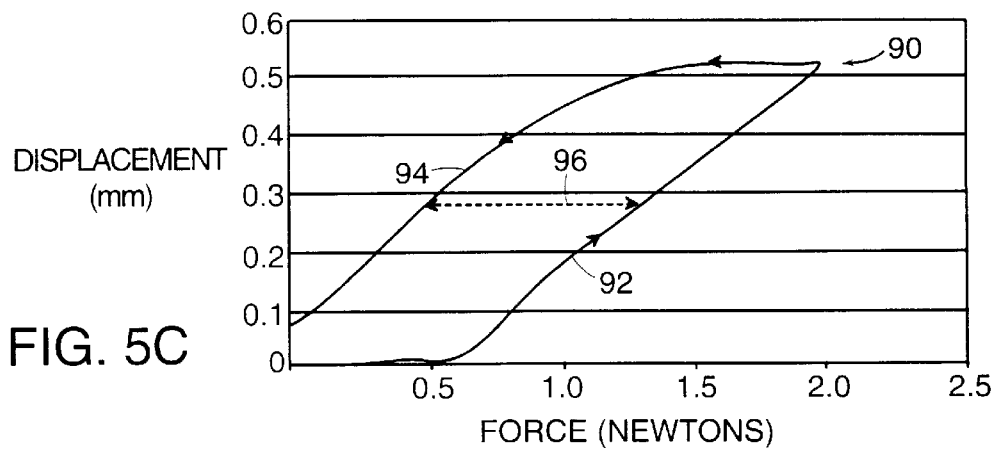

Referring to FIGS. 5A–5C, a series of graphs relating to compressive property measurements for a silicone rubber sample using indentor instrument 2 are shown. In performing the measurement, a sinusoidal force was applied to the sample, the frequency of the sinusoidal force increasing from 1 Hertz to 10 Hertz. One force cycle was applied at each frequency and the frequency was increased by 1 Hertz in each subsequent cycle. The overall measurement lasted less than 3 seconds. The data in FIGS. 5A–5C was collected over the 1 Hertz cycle.

Referring to FIG. 5A, curve 80 represents a typical compressive force characteristic (Y-axis), in units of Newtons, applied by voice coil actuator 30 as a function of time. For the particular silicone rubber sample under test, control unit 16 is adjusted to provide an electrical signal to voice coil actuator 30, so that a compressive force having a maximum amplitude of 2 Newtons is applied to the sample over a 1 second cycle.

Referring to FIG. 5B, the silicone rubber sample deforms in response to applying the compressive force shown in FIG. 5A. Curve 82 represents the displacement characteristic (Y-axis) in units of mm as a function of time and over the same 1 second cycle of FIG. 5A. Curve 82 shows that at the beginning of the cycle, a region 84 of little or no displacement is observed. This may be caused, for example, by sources of friction associated with the motion of probe 8 (e.g., probe sliding within sleeve bearing 41). Before probe 8 starts to move, frictional forces between moving parts must be overcome. Thus, no displacement occurs until the time at which the force applied to probe 8 is greater than the frictional force. At a point 86, and over the next 0.25 seconds, the displacement steadily increases until it approaches a maximum of about 0.52 mm. The displacement then maintains a relatively constant value for about 0.3 seconds before dropping to a displacement value of about 0.07 mm at point 88 near the end of the cycle. This displacement value represents the deformation of the sample in the absence of an applied force and may be indicative of a viscoelastic effect (described further below) occurring in the silicone rubber sample. The displacement value may also be due, in part, to the frictional forces acting to resist the motion of probe 8 as it returns to its initial reference position.

Referring to FIG. 5C, data from curves 80 and 82 of FIGS. 5A and 5B, respectively, are used by control unit 16 to generate a displacement-force characteristic curve 90 for the rubber sample. Curve 90 represents the change in the displacement over the range of applied compressive force shown in FIG. 5A and is useful in characterizing the stiffness and resiliency of the sample (i.e. the ability of a material to recover from an applied force).

For example, initially, curve 90 follows a path 92 as force is increased from 0 Newtons to 1.75 Newtons (arrows show increasing time on the graph). The slope of path 92 is related to the stiffness of the sample. In particular, when the slope of path 92 has a high value, the change in displacement is large for a given increase in compressive force. This behavior is characteristic of a low stiffness material. Alternatively, when the slope of path 92 has a low value, the change in displacement is small over the same given increase in compressive force, a behavior characteristic of a high stiffness material.

The slope of path 92 is relatively constant up to 1.75 Newtons, the maximum force, at which point the maximum displacement of 0.52 mm is reached. As the force is decreased, the displacement does not follow path 92 but remains at approximately 0.52 mm for a time period of about 0.3 seconds (FIG. 5B) and follows a second path 94. This behavior is known as hysteresis. The observed hysteresis may be the result of the inability of the silicone rubber sample to instantaneously recover from, or respond to, the compressive force. The response of the sample is time-dependent, which is a characteristic of a viscoelastic material. The resiliency of a material is related to the amount of hysteresis and can be approximated by measuring a separation between path 92 and path 94 at a given displacement, e.g., that indicated by dashed line 96.

Figure 6:
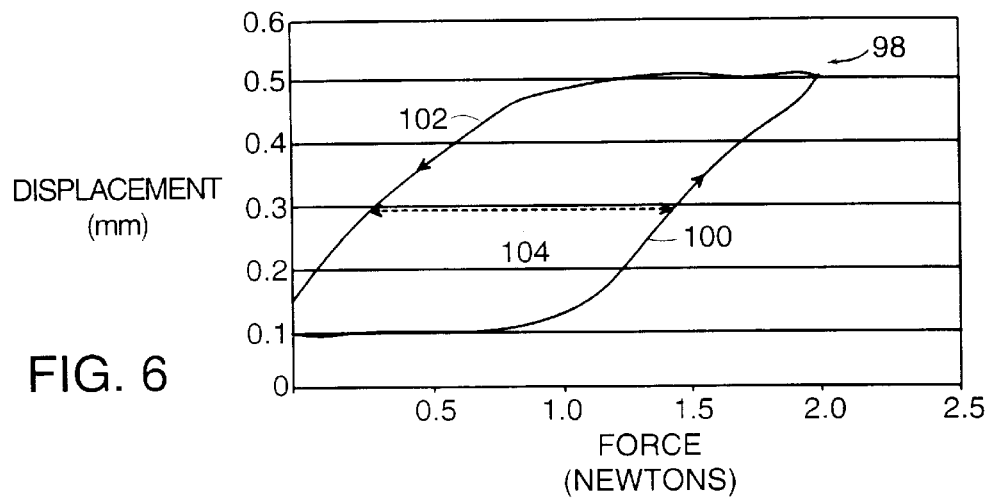
FIG. 6 is a displacement-force graph of the silicone rubber sample during a 10 Hertz cycle of the measurement.

Referring to FIG. 6, a curve 98 representing displacement of the same sample as a function of applied compressive force is shown measured for a 10 Hz cycle. The displacement versus force graph at 10 Hz also shows hysteresis. As force is increased to 2 Newtons, the displacement follows a path 100 and, as force is decreased, the displacement returns along a path 102.

Several differences are observed between curve 90 of FIG. 5C measured at 1 Hertz and of FIG. 6 measured at 10 Hertz. The slope of path 100 (FIG. 6) differs from the slope of path 92 (FIG. 5C) and thus, the measured stiffness of the silicone rubber sample is frequency dependent. The hysteresis of the curve at 10 Hertz, approximated by the separation indicated by dashed line 104, is greater than the separation of curve 90. The greater hysteresis is indicative of a slower recovery at the high frequency. The variation of displacement-force curves at different frequencies are a characteristic of the sample being measured. Thus, the frequency signatures of a material may be evaluated to determine suitability of the material as a replacement for another material having its own frequency signature. For example, the frequency signature of a candidate replacement material and healthy articular cartilage may be compared.

Figure 7:
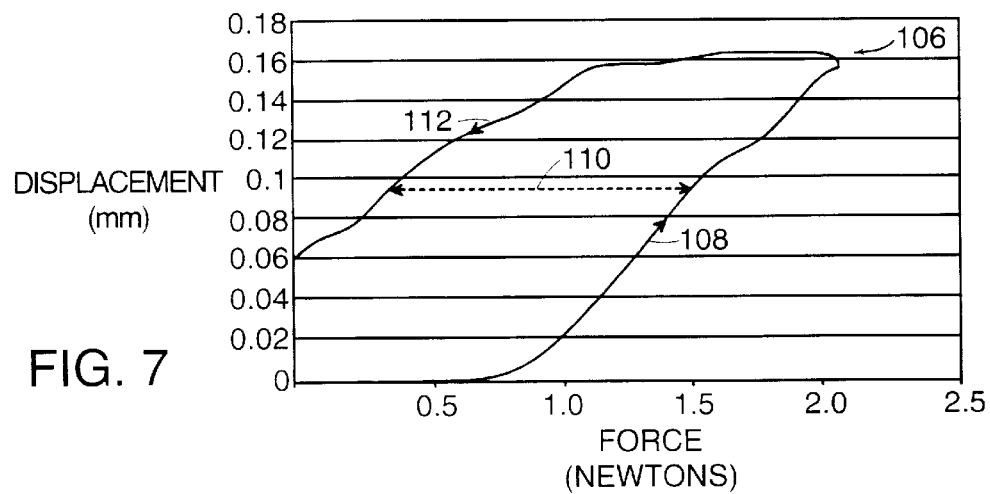
FIG. 7 is a graph of data obtained during the measurement of the compressive properties of a cow cartilage sample.

As described above for the silicone rubber sample, a sinusoidal force was applied to the cow cartilage sample with the frequency increasing from 1 Hz to 10 Hz during the measurement. Referring to FIG. 7, a force displacement curve 106 measured at 1 Hz is shown for a sample of cow cartilage measured with the indentor instrument.

The stiffness of the cartilage at 1 Hz is characterized by the slope of a path 100 in the direction of increasing force. By comparing the slope of path 108 to the slope of path 92

(FIG. 5C), it is observed that the cow cartilage sample is stiffer than silicone rubber. Accordingly, the maximum deformation of the cow cartilage sample, which occurs at 2 Newtons, is approximately 0.165 inches which is significantly less than the maximum deformation 0.52 mm of the silicone rubber sample.

The resiliency of the cow cartilage at 1 Hz is characterized by the degree of hysteresis, which is approximated by the separation indicated by dashed line 110 between paths 108 and 112 of increasing and decreasing forces, respectively. By comparing the separations between FIG. 5C and FIG. 7, it is observed that, at 1 Hz, the silicone rubber has slightly less hysteresis and thus recovers slightly faster the cow cartilage sample.

What is claimed is:

1. An instrument for measuring the compressive properties of a body comprising:
   an elongated probe having a longitudinal axis and a distal end configured to contact the body;
   a biasing assembly, mechanically coupled to the elongated probe, for applying a constant pre-determined pre-load to the body to establish a measurement reference at the predetermined pre-load;
   an actuator for moving the distal end of the elongated probe along the longitudinal axis to apply a variable compressive force to the body, the actuator configured to apply the variable compressive force after the measurement reference has been established; and
   a measurement device, coupled to the elongated probe, for measuring displacement of the elongated probe along the longitudinal axis in response to the variable compressive force relative to the measurement reference.

2. The instrument of claim 1 wherein the biasing assembly includes a moveable member coupled to a biasing element.

3. The instrument of claim 2 wherein the moveable member includes a sheath surrounding the elongated probe.

4. The instrument of claim 3 wherein the biasing assembly includes a constant force spring connected to the sheath.

5. The instrument of claim 2 wherein the actuator and the measurement device are included within a piston assembly moveable within the housing.

6. The instrument of claim 1 wherein the actuator is a voice-coil actuator.

7. The instrument of claim 5 wherein the actuator is configured to apply a variable force having a magnitude which varies sinusoidally.

8. The instrument of claim 7 wherein the actuator is adapted to vary the magnitude of the sinusoidally-varied force between 1 and 10 Hertz.

9. The instrument of claim 1 wherein the measurement device is adapted to provide an output signal proportional to the displacement of the elongated probe.

10. The instrument of claim 9 wherein the measurement device includes a linear variable differential transformer.

11. The instrument of claim 1 further comprising a housing having a handle for manipulating the instrument, the housing enclosing the biasing element, the actuator, and the measurement device.

12. The instrument of claim 1 further comprising a data acquisition system that collects an output signal proportional to the displacement of the elongated probe.

13. The instrument of claim 12, wherein the data acquisition system collects an output signal proportional to the compressive force applied to the body.

14. The instrument of claim 13, wherein the data acquisition system generates data relating the output signal proportional to the displacement of the elongated probe to the output signal proportional to the compressive force applied to the body.

15. The instrument of claim 12, wherein the data acquisition system generates data relating the output signal proportional to the displacement of the elongated probe to a known compressive force signature applied to the body.

16. The instrument of claim 1, wherein the actuator reciprocates the distal end of the elongated probe.

17. A method of measuring the compressive properties of a body comprising:
    establishing a measurement reference by applying a constant pre-determined pre-load to the body with a biasing assembly;
    positioning a distal end of an elongated probe to contact the body;
    applying a variable compressive force to the body by moving the distal end of the elongated probe along a longitudinal axis of the elongated probe; and
    measuring displacement of the elongated probe along the longitudinal axis, relative to the measurement reference, in response to the variable compressive force applied to the body.

18. The method of claim 17, wherein applying the compressive force includes applying a variable force.

19. The method of claim 18, further comprising collecting an output signal proportional to the compressive force applied to the body.

20. The method of claim 19, further comprising generating data relating the output signal proportional to the displacement of the elongated probe to the output signal proportional to the compressive force applied to the body.

21. The method of claim 20, further comprising comparing, with a processor unit, output signals from the body to output signals from a healthy cartilage sample.

22. The instrument of claim 21, wherein the actuator is adapted to vary the magnitude of the sinusoidally-varied force between 1 and 10 Hertz.

23. The method of claim 19, further comprising displaying, on a monitor, data relating to at least one of the applied compressive force and measured displacement.

24. The method of claim 17, further comprising collecting an output signal proportional to the displacement of the elongated probe.

25. The method of claim 24, further comprising generating data relating the output signal proportional to the displacement of the elongated probe to a known compressive force signature applied to the body.

26. The instrument of claim 25, wherein the actuator is configured to apply a variable force having a magnitude which varies sinusoidally.

27. An instrument for measuring the compressive properties of a body comprising:
    an elongated probe having a longitudinal axis and a distal end configured to contact the body;
    a biasing assembly including a force actuator connected to a sheath surrounding the elongated probe, wherein the biasing assembly is mechanically coupled to the elongated probe and the force actuator is configured to apply a pre-determined pre-load to the body to establish a measurement reference at the predetermined pre-load;
    an actuator configured to reciprocate the distal end of the elongated probe along the longitudinal axis to apply a variable compressive force to the body through the distal end; and
    a measurement device, coupled to the elongated probe, for measuring displacements of the elongated probe along the longitudinal axis in response to the variable compressive forces relative to the measurement reference.

* * * * *

UNITED STATES PATENT AND TRADEMARK OFFICE
CERTIFICATE OF CORRECTION

PATENT NO. : 6,068,604  
DATED : May 30, 2000  
INVENTOR(S) : Kenneth W. Krause

Page 1 of 1

It is certified that error appears in the above-identified patent and that said Letters Patent is hereby corrected as shown below:

Column 7,  
Line 25, replace "Figs. 5A-SC" with -- Figs. 5A-5C --.  
Line 33, replace "Figs. 5A-SC" with -- Figs. 5A-5C --.

Signed and Sealed this

Twenty-fifth Day of December, 2001

Attest:

Attesting Officer

JAMES E. ROGAN  
Director of the United States Patent and Trademark Office